US00PP10830P

United States Patent [19]

Fleming

[11] Patent Number: Plant 10,830

[45] Date of Patent: Mar. 16, 1999

[54] KALANCHOE PLANT NAMED 'ROCKET'

[75] Inventor: Margaret Marne Fleming, Soquel, Calif.

[73] Assignee: The Plant Co., Half Moon Bay, Calif.

[21] Appl. No.: 938,577

[22] Filed: Sep. 26, 1997

[51] Int. Cl.[6] ..... A01H 5/00

[52] U.S. Cl. ..... Plt./87.15

[58] Field of Search ..... Plt./87.15

*Primary Examiner*—Howard J. Locker

*Attorney, Agent, or Firm*—C. A. Whealy

[57] ABSTRACT

A distinct cultivar of Kalanchoe plant named 'Rocket', characterized by its bright deep crimson flower color; upright plant habit; relative compactness; freely branching habit with shoots forming at every node; uniform plant habit and inflorescence display; small dark green glossy leaves; proportional leaf size to plant size; numerous flowers per plant; medium to large flowers; resistance to Botrytis, Rhizoctonia and Fusarium; and excellent postproduction longevity.

1 Drawing Sheet

The present invention relates to a new and distinct cultivar of Kalanchoe plant, botanically known as *Kalanchoe blossfeldiana* Adans., and hereinafter referred to by the cultivar name 'Rocket'.

The new cultivar is a product of a planned breeding program conducted by the inventor in Soquel and Half Moon Bay, Calif. The objective of the breeding program was to create new Kalanchoe cultivars having a uniform and compact plant habit; freely branching habit; attractive flower and foliage colors; short response time; resistance to deseases and insects; and good postproduction longevity.

The new cultivar originated from a self-pollination made by the inventor of a proprietary *Kalanchoe blossfeldiana* Adans. selection code number 967-001. The cultivar 'Rocket' was discovered and selected by the inventor in July, 1993, as a flowering plant within the progeny of the stated selfing in a controlled environment in Soquel, Calif. Compared to the parent selection, plants of the new Kalanchoe are larger, flower one week later, have larger leaves and have a different flower color.

Asexual reproduction of the new cultivar by terminal and node cuttings taken at Soquel and Half Moon Bay, Calif., has shown that the unique features of this new Kalanchoe are stable and reproduced true to type in successive generations.

The cultivar Rocket has not been observed under all possible environmental conditions. The phenotype may vary somewhat with variations in environment such as temperature, daylength and light intensity, without, however, any variance in genotype.

The following traits have been repeatedly observed and are determined to be the unique characteristics of 'Rocket'. These characteristics in combination distinguish 'Rocket' as a new and distinct cultivar:

1. Bright deep crimson flower color.
2. Upright plant habit, relatively compact.
3. Full plants, freely branching habit with shoots forming at every node. Plants do not require pinching.
4. Uniform plant habit and inflorescence display.
5. Small dark green glossy leaves.
6. Proportional leaf size to plant size.
7. Numerous flowers per plant.
8. Medium to large flowers.
9. Resistant to Botrytis, Rhizoctonia and Fusarium.
10. Not attractive to aphids.
11. Excellent postproduction longevity.

The new Kalanchoe is most similar in flower color to the commercial cultivar, Juliana (disclosed in U.S. Plant Pat. No. 02010,228).

However, in side-by-side comparisons in Soquel and Half

Moon Bay, Calif., plants of the new Kalanchoe were more freely branching; more compact; and had smaller leaves than plants of the cultivar Juliana. Although flower color of plants of the cultivar Juliana is similar to flower color of plants of the new Kalanchoe, there is a discernible difference in the shade of the color. In addition, under high light, foliage of plants of the cultivar Juliana will become red, whereas under high light, foliage of plants of the new Kalanchoes will maintain remain dark green without reddening.

BRIEF DESCRIPTION OF THE PHOTOGRAPH

The accompanying colored photograph illustrates the overall appearance of the new cultivar, showing the colors as true as it is reasonably possible to obtain in colored reproductions of this type. The photograph comprises a top perspective view of a typical potted plant of 'Rocket' taken in Soquel, Calif. Flower color in the photograph may appear different from the actual color due to light reflectance.

DETAILED BOTANICAL DESCRIPTION

In the following description, color references are made to The Royal Horticultural Society Colour Chart except where general terms of ordinary dictionary significance are used. Measurements and numerical values represent typical plants in 10.5-cm containers that were grown during the spring in Northern California. Plants were grown under cultural and environmental conditions that approximated commercial practice in a plastic-covered greenhouse with day temperatures ranging from 16 to 38° C. and night temperatures ranging from 4.5 to 13° C. Plants were exposed to five weeks of long day/short nights followed by six weeks of short day/long night photoperiodic treatments.

Botanical classification: *Kalanchoe blossfeldiana* Adans. cultivar 'Rocket'.

Parentage:

*Male or pollen parent.*—Proprietary *Kalanchoe blossfeldiana* Adans. selection code number 967-001.

*Female or seed parent.*—Proprietary *Kalanchoe blossfeldiana* Adans. selection code number 967-001.

Propagation:

*Type cutting.*—Terminal cuttings.

*Time to initiate roots.*—10 to 12 days at 21° C. soil temperature.

*Time to develop roots.*—About 20 days at 18° C. soil temperature.

*Rooting habit.*—Numerous, fine, fibrous, and well-branched.

Plant description:

*Form.*—Upright and uniform. Relatively compact. Plant shape is an inverted triangle with a rounded apex.

*Branching habit.*—Freely branching, generally shoots formed at every node. Plants do not require pinching.

*Plant height at flowering.*—About 18 cm from soil level to top of plant, about 18 cm in diameter, appropriate for 10.5-cm and smaller containers.

*Vigor.*—Moderately vigorous and moderate growth rate.

*Production time.*—Three to 6 weeks of long day/short night conditions followed by about 6 weeks of short day/long night conditions are required to initiate and develop flowers. Plants are in flower 4 to 5 weeks later. Depending on environmental conditions, a total of 13 to 17 weeks is required.

*Foliage description.*—Leaves simple, opposite, generally symmetrical. Length: About 5.5 cm. Width: About 4.75 cm. Shape: Ovate. Apex: Rounded. Base: Obtuse to cordate. Margin: Crenate. Texture: Leathery, glabrous, glossy, coriaceous and succulent. Petiole length: About 1.2 cm. Color: Young foliage upper surface: 147A. Young foliage lower surface: Darker than 146A. Mature foliage upper surface: 147A. Mature foliage lower surface: 147B. Petiole: 146A. Stem color: 144A.

Flower description:

*Flower type and habit.*—Single flowers arranged in compound dichasial cymes on strong peduncles. Freely flowering and very floriferous with new buds continuing to develop. Uniform inflorescence display.

*Natural flowering season.*—Plants flower under natural daylengths during the autumn and winter. Flower initiation and development can be induced under short day/long night conditions. After induction, opening of new buds continuous. Flowers persistent.

*Inflorescences borne.*—Above foliage, arising from leaf axils. Inflorescence of each shoot is formed by dichotomous branching.

*Time to flower.*—Under optimal environmental and culural conditions, plants of the cultivar Rocket will start flowering after 10 or 11 weeks after start of controlled photoperiods (short day/long night conditions). First flower open is the terminal flower at the main axis and is followed by the opening of the terminal flowers of the side branches of the inflorescence.

*Flower diameter.*—About 1.7 cm.

*Flower depth* (*height*).—About 1.2 cm.

*Quantity.*—More than 125 flowers per plant.

*Flower buds.*—Length: About 1.2 cm. Width: About 4 mm. Shape: Oblong becoming tubular/ovoid with development. Rate of opening: Rapid. Color: Initialy green, 144A, becoming red green just before opening, then red, 45A.

*Petals.*—Quantity: Four. Length: About 7 mm. Width: About 6 mm. Shape: Rounded. Apex: Acuminate. Margin: Entire. Texture: Glabrous, smooth and satiny. Aspect: Flat. Color: When opening, upper surface: 45A. When opening, lower surface: Light pink with red, 45A, streaks. Mature, upper surface: 45A. Mature, lower surface: Light pink with red, 45A, streaks. Throat: Light green, 144B, translucent. Tube: Light green, 144A, translucent.

*Sepals.—Quantity: Four. Length: About* 6 mm. Width at base: About 2 mm. Shape: Linear. Apex: Pointed. Margin: Entire. Texture: Glabrous. Aspect: Upright. Color: 144A.

*Peduncle.*—Aspect: Strong, erect, rigid, and upright. Length: About 4 mm. Texture: Glabrous. Color. 146A.

*Reproductive organs.*—Stamens: Stamen number: Eight. Anther size: About 0.4 mm. Anther shape: Flat, oblong. Pollen color: Yellow, close to 12B. Amount of pollen: Moderate. Pistils: Pistil number: Four. Stigma shape: Flat. Stigma color: Light yellow, close to 9D. Style length: About 9 mm. Style color: 144A. Ovary number: Four-celled.

Disease resistance: Plants of the new Kalanchoe have been observed to be resistant to Botrytis, Rhizoctonia and Fusarium.

Insect resistance: Plants of the new Kalanchoe are not attractive to aphids.

Seed production: Seed production has not been observed.

It is claimed:

1. A new and distinct cultivar of Kalanchoe plant named 'Rocket', as illustrated and described.

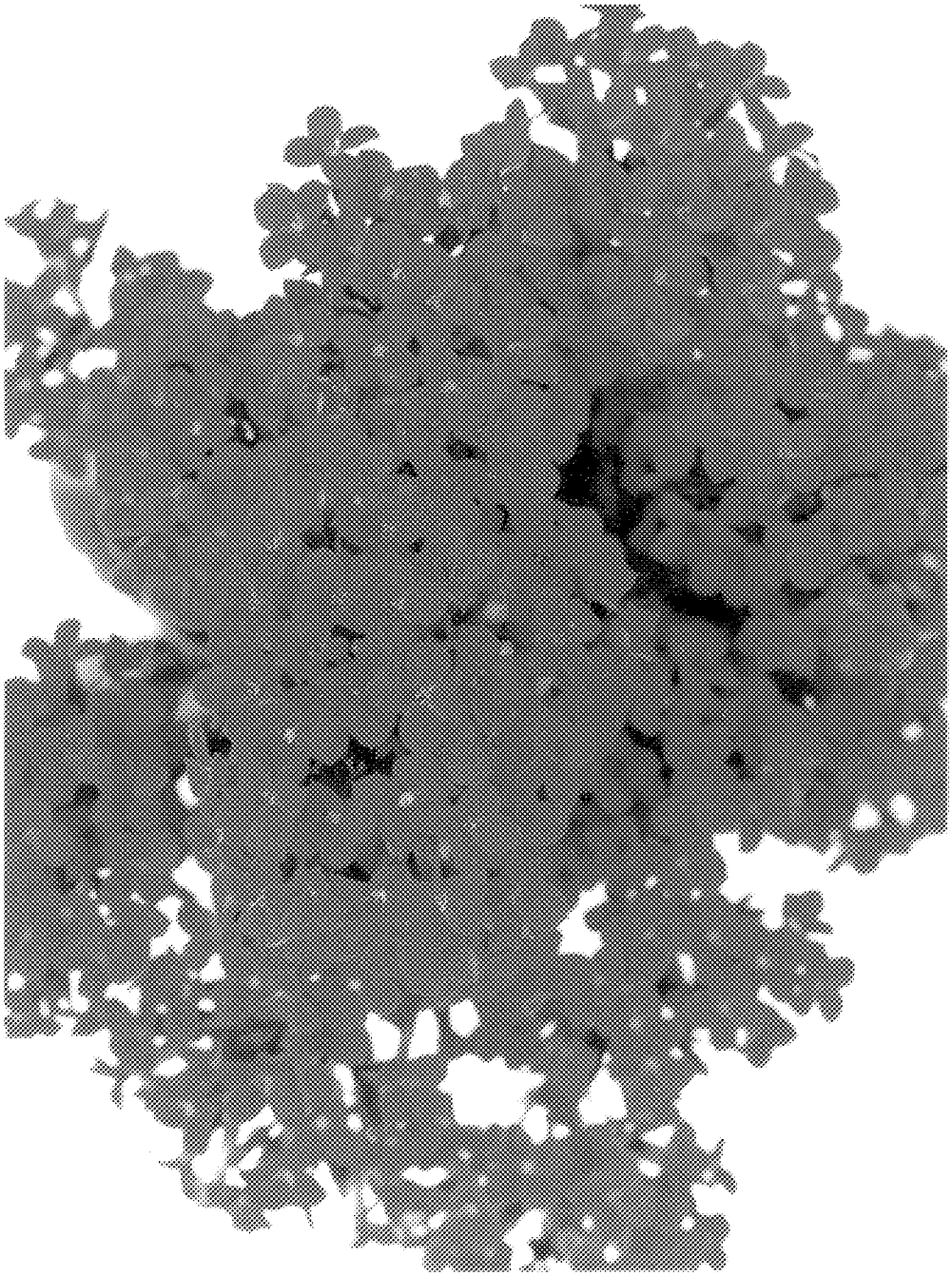

* * * * *